United States Patent [19]

Cooper

[11] Patent Number: 5,050,620

[45] Date of Patent: Sep. 24, 1991

[54] ANKLE BRACE

[76] Inventor: Ronald L. Cooper, 16305 W. 141st St., Olathe, Kans. 66062

[21] Appl. No.: 534,462

[22] Filed: Jun. 7, 1990

[51] Int. Cl.⁵ .............................................. A61H 5/00
[52] U.S. Cl. ............................... 128/80 H; 128/80 R; 128/882
[58] Field of Search ................... 128/80 R, 80 H, 882

[56] References Cited

U.S. PATENT DOCUMENTS

| | | |
|---|---|---|
| 4,280,489 | 7/1981 | Johnson . |
| 4,495,942 | 1/1985 | Palumbo .......................... 128/80 H |
| 4,517,968 | 5/1985 | Green et al. ...................... 128/80 H |
| 4,729,370 | 3/1988 | Kallassy . |
| 4,864,741 | 9/1989 | Beauchemin ................. 128/80 H X |
| 4,865,023 | 9/1989 | Craythorne et al. ............. 128/80 H |
| 4,869,267 | 9/1989 | Grim et al. ....................... 128/80 H |

OTHER PUBLICATIONS

Med Spec—Ankle Stabilizing Orthosis—advertising flyer.
Action Dynamics, Inc.—ADA Brace—advertising flyer.
Duo-Loc—Ankle Support—advertising flyer—1990.
Airprene—Ankle Supports—Advertising flyer.
Cramer Sports Medicine—1990 Catalog—Ankle Stabilizer—p. 13.

Primary Examiner—Robert A. Hafer
Assistant Examiner—Kerry Owens
Attorney, Agent, or Firm—Hovey, Williams, Timmons & Collins

[57] ABSTRACT

An ankle brace is provided with a stretchable, padded underliner which is open at the front to receive the wearer's foot and close therearound. A medial strap and a lateral strap are attached to the underliner at the sole portion thereof, and are provided with remote ends which are to be pulled upwardly to place tension on opposite sides of the foot and ankle and thus, when attached to the underliner, bias the foot to a neutral position. The alignment of the straps from the sole of the underliner to the inside and outside of the underliner proximate the ankle serve to support the ankle without the application of torsion thereto. At least one wrap extends circumferentially around the underliner proximate the ankle in covering relationship to the medial and lateral straps as an aid in holding them in place. The ankle brace may be used with either foot and with conventional footwear.

9 Claims, 3 Drawing Sheets

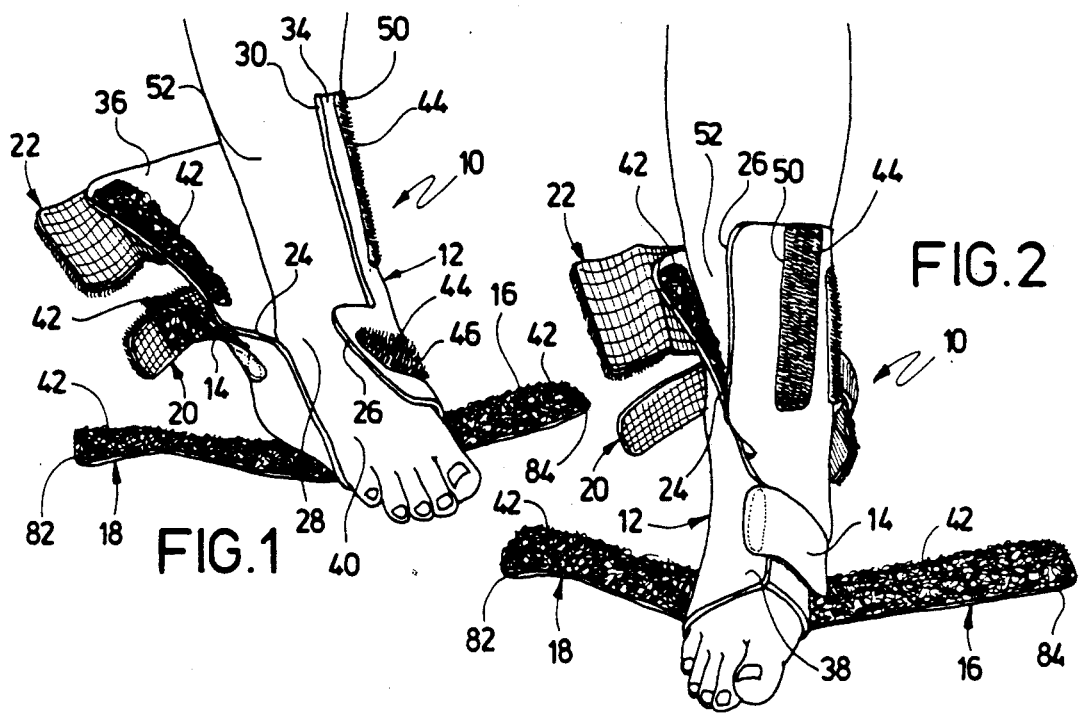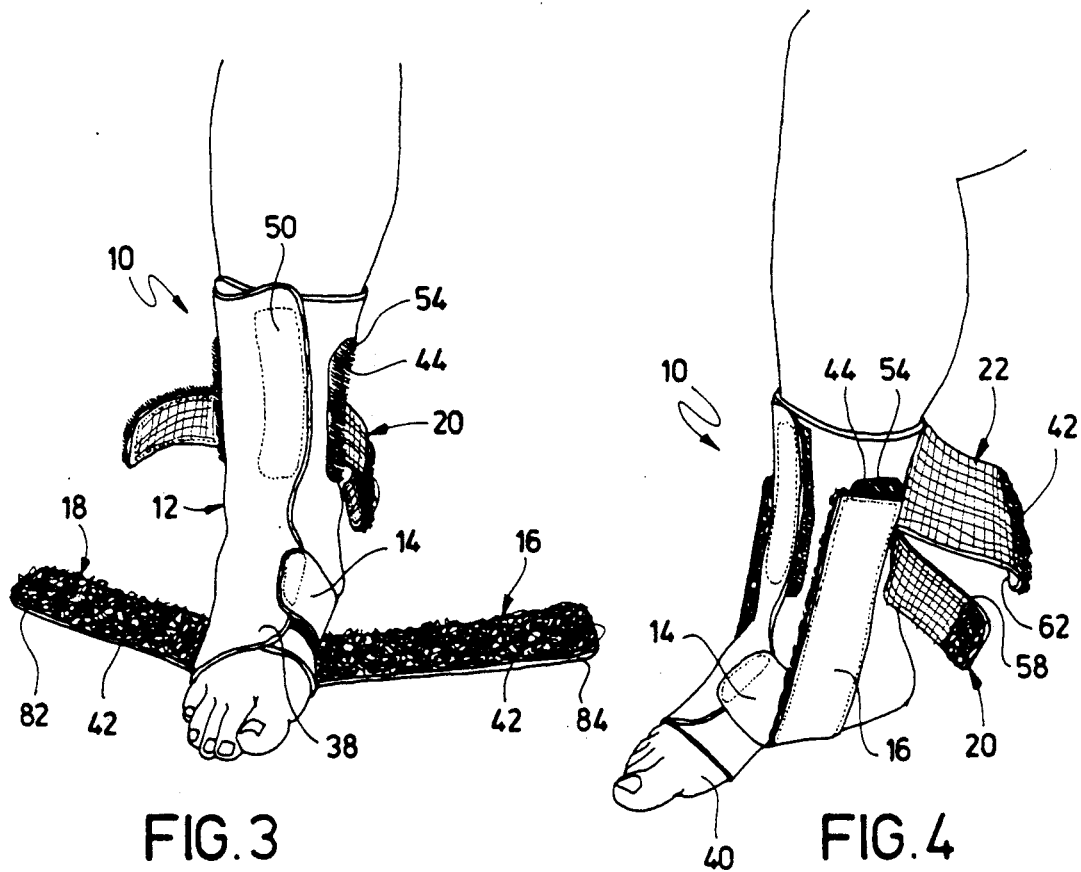

ANKLE BRACE

BACKGROUND OF THE INVENTION

1. Field of the Invention

This invention concerns an ankle brace which enables the wearer to participate in normal athletic events while protecting an injured or susceptible ankle from further injury by supporting both the inner and outer portions of the foot and ankle without imposing relative twisting forces between the ankle and foot.

2. Description of the Prior Art

During the course of routine activities or athletic endeavors, the human ankle is subjected to various shocks and strains which may cause an injury such as a sprain. To allow continued activity of a person having an injured ankle or as a prophylactic measure against injury, adhesive tape has heretofore been used to wrap an ankle. Unfortunately, tape must be discarded after each use and considerable time and expense may be incurred in repeated taping of the ankle. In addition, the tape is often inflexible and results in discomfort and loss of motion during wear, as well as being somewhat difficult to remove.

As a result of these disadvantages, efforts have been made to develop a support or brace for the ankle which is more permanent, which is to say removable, and therefore more economical. Such braces must necessarily be designed for enabling the wearer to wear his or her existing shoes and thus must be closely conforming to the foot. Existing ankle braces include webs which may be laced in the manner of conventional shoes and are provided with straps which wrap across the instep. Other models have lateral straps which are inelastic and places tension on the foot, such as that shown in U.S. Pat. No. 4,729,370 to Kallassy.

While such ankle braces have proven to be a general improvement over the use of adhesive tape, they have tended to place tension on the foot causing it to turn relative to the leg. Because of the tension applied to the medial side of the foot, they have tended to lead the foot of the wearer into a condition of inversion — that is that the outside of the foot is pulled downwardly placing greater strain on the ankle. In addition, such prior art ankle braces are designed for either the right or the left foot and may not be used with either foot.

SUMMARY OF THE INVENTION

The ankle brace of the present invention overcomes these problems by a support system which allows support of the ankle with the foot biased to a neutral position and not angled relative to the leg or may be adjusted to permit inversion or eversion of the foot as desired. In addition, the ankle brace hereof is configured for use with either foot and provides additional support for the ankle by lateral and medial straps which wrap under the foot and are covered by a protective wrap.

In accordance with these and other objects of the invention, the ankle brace of the present invention broadly includes an underliner which is generally open along the front to receive therein the wearers foot, ankle and lower leg and wrap therearound. A medial strap is attached to the sole portion of the underliner and extends upwardly along the inside of the leg to provide support for the medial ligaments. Similarly, a lateral strap extends upwardly along the outside of the ankle and leg to provide support for the lateral ligaments. Each of the straps are oriented on the underliner to provide maximal and proper direction of force. The straps are attached to the underliner along the sides of the wearers lower leg and then covered by a pair of circumferentially extending wraps which surround the lower leg adjacent and immediately above the ankle. This overlapping of the wrap over the straps provides a basketweave type of support for both the lateral and medial ligamentous structures.

The closures for securing the underliner in position and for holding the straps and wrap in position are preferably hook and pile fabric, such as that sold under the trademark VELCRO. The ankle brace is thereby adjustable for a range of foot sizes and the strap extending along the lateral portion of the ankle may be adjustably tensioned according to the needs of the wearer while the medial portion may be attached without tension. Both the medial and lateral portions of the strap originate from the plantar aspect of the midfoot, allowing for control of both inversion and eversion sprain mechanisms. The brace thus allows for active eversion under adjustable tension to prevent inversion of the foot, unique to the inversion sprain mechanism, or alternately may bias the foot to a neutral position by placing equal tension on both medical and lateral straps for treatment of eversion sprains. The underliner extends from the base of the calf to the metatarsal head, thereby providing a maximum base of support.

The forward placement of the origin of the medial and lateral straps not only allows the ankle brace hereof to be used for either foot, but also will maintain the neutral, right-angle flexion position of the foot relative to the ankle for immobilization during initial treatment of an ankle sprain. Because of its relatively thin profile and construction, it may be used with existing footwear in the home, general working environment, or in athletics, and thus be suitable for wearers with either acute or chronic ankle problems.

BRIEF DESCRIPTION OF THE DRAWINGS

FIG. 1 is a left front perspective view of the ankle brace in accordance with the present invention, showing the underline opened after receiving a foot of a wearer therein;

FIG. 2 is a front perspective view of the ankle brace hereof with the instep strap secured;

FIG. 3 is a front perspective view similar to FIG. 2 but with the underliner wrapped to a closed position;

FIG. 4 is a right perspective view of the ankle brace hereof showing the medial strap secured along the medial side of the wearer's ankle;

DESCRIPTION OF THE PREFERRED EMBODIMENT

Figure 5:
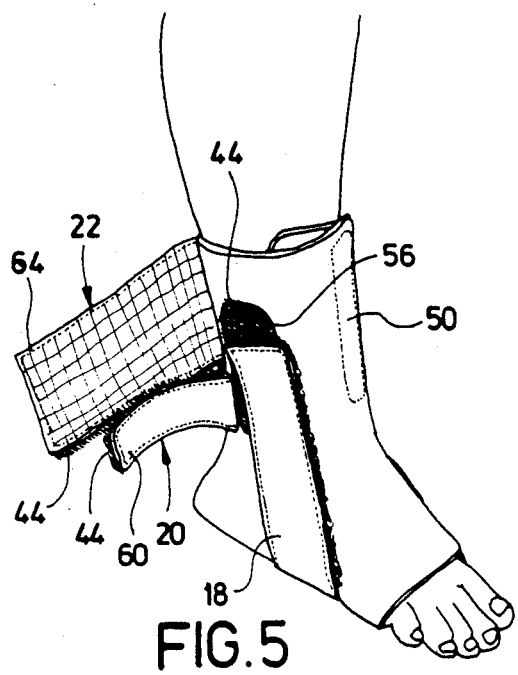
FIG. 5 is a left front perspective view of the ankle brace hereof showing the lateral strap secured along the lateral side of the wearer's ankle.
Figure 6:
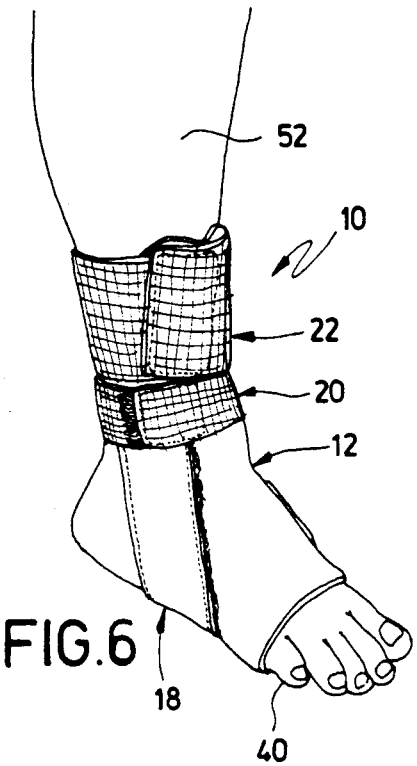
FIG. 6 is a left front perspective view similar to FIG. 5 and showing the ankle brace hereof in a fully wrapped condition with the upper and lower leg straps closed around the medial strap.
Figure 7:
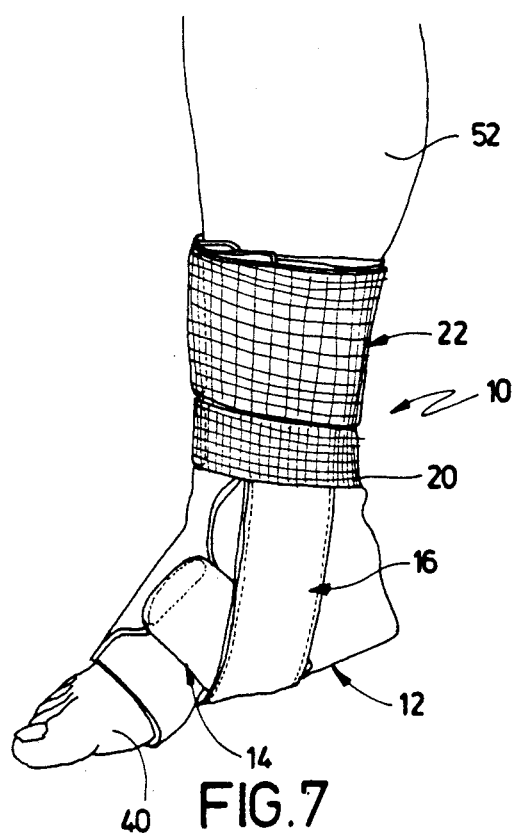
FIG. 7 is a right front perspective view showing the ankle brace hereof in a fully wrapped condition.
Figure 8:
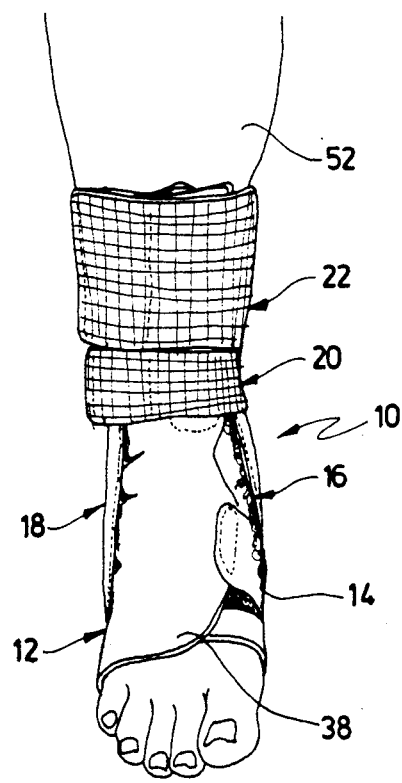
FIG. 8 is a front perspective view showing the ankle brace hereof in a fully wrapped condition.

Referring now to the drawing an ankle brace 10 in accordance with the present invention broadly includes an underliner 12, an instep strap 14, a medial strap 16, a lateral strap 18, a lower leg wrap 20 and an upper leg wrap 22. The underliner 12 presents an opening defined by left front margin 24 and right front margin 26 for receiving therethrough the wearer's ankle 28.

Figure 9:
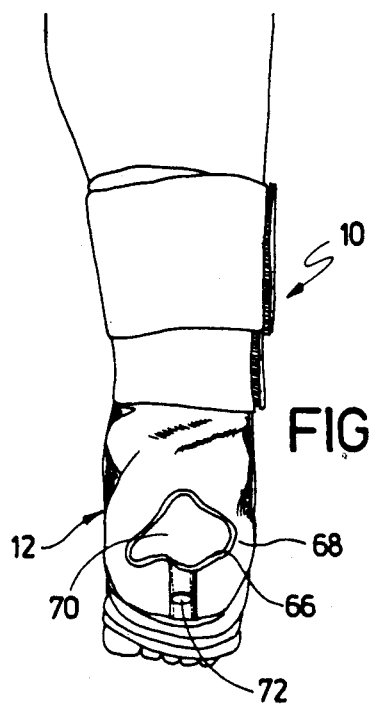
FIG. 9 is a rear elevational view of the ankle brace hereof showing an opening in the rear of the underliner through which a heel cup may be seen.
Figure 10:
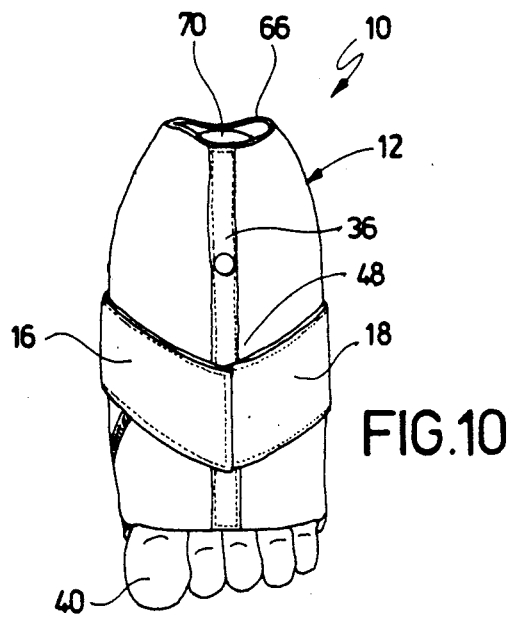
FIG. 10 is a rear bottom perspective view showing the bottom of the ankle brace hereof and a rivet for mounting a heel cup interior to the underliner.
Figure 11:
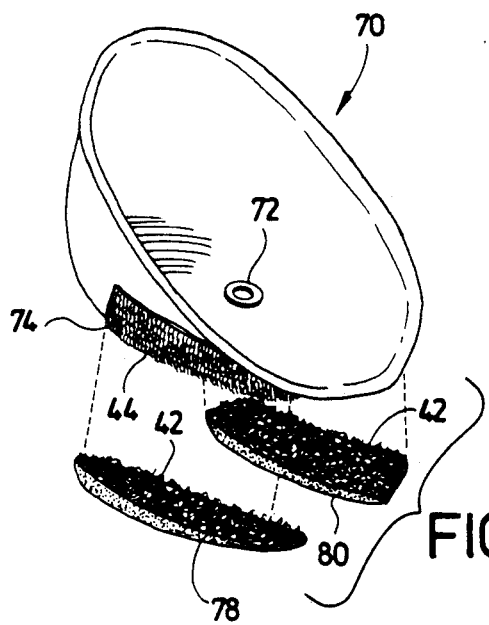
FIG. 11 is a right front perspective view of the heel cup and foam heel counters used with the invention hereof.
Figure 12:
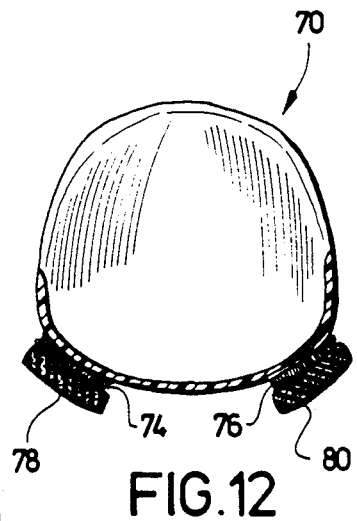
FIG. 12 is a front cross-sectional view through the heel cup and heel counters used with the ankle brace hereof.

In greater detail, underliner 12 is preferably cut to the appropriate size of a single sheet of elastomeric, padded material. Such material is preferably open-celled foam 30 nominally approximately one-eighth inch thick bonded to a flexible, elastic inner fabric web 32 and a flexible, elastic outer fabric web 34 which permits the open-celled foam 30 to ventilate the wearer's ankle 28. The underliner 12 is cut to fit the wearer's ankle 28 and sewn along a bottom seam 36 as best seen in FIGS. 9 and 10 to present a unitary, foot conforming structure.

Left margin 24 includes a tongue 38 which is sized and oriented for extending over the metatarsal region of the wearer's foot 40. Attached to the tongue 38 by sewing or the like is instep strap 14, which is provided with pile material 42 on the interior for attachment to hook material 44 sewn on the underline 12 adjacent right front margin 26 whereby a first closure region 46 is provided.

Lateral strap 18 and medial strap 16 are elongated strips of flexible relatively inelastic material attached to the underside of underliner 12 by sewing along bottom seam 36. The lateral and medial straps may be formed of a single strip of inelastic material sewn at the midpoint thereof to the bottom seam 36 of the underliner 12. As may be seen in FIGS. 9 and 10, the lateral strap 18 and medial strap 16 are secured to the underliner 12 at the sole 48 of the ankle brace 10 adjacent the arch of the wearer's foot 40. The lateral strap 18 is provided with a remote end 82, and medial strap 16 is provided with a remote end 84; both remote end 82 and remote end 84 having pile material 42 on the interior thereof as viewed when each is attached to the underliner 12.

As may be seen in FIGS. 1 and 2, a second closure region 50 is defined adjacent left margin 24 and right margin 26 along the lower leg 52 of the wearer by pile material 42 attached to the interior of the underliner adjacent the left margin and hook material 44 attached to the exterior of the underliner 12 adjacent the right margin. The hook and pile material is sewn to the underline 12 whereby the first closure region 46, shown in FIG. 3 is the area where the medial strap 14 overlaps onto the pile material 44 while the second closure region 50 is defined where the pile material 42 adjacent the lower leg 52 overlaps the hook material 44.

A medial strap attachment region 54 is located along thhe inside of the wearer's ankle 28 as seen in FIGS. 3 and 4. Region 54 is provided with hook material 44 for receiving the pile material 42 of medial strap 16 for engagement therewith. Similarly, as shown in FIG. 5, a lateral strap attachment region 56 is located along the outside of the wearer's ankle 28 and is defined by an area of hook material 44 sewn on the outside of the underliner 12. Additional areas of hook material 44 may be sewn along the exterior of the underliner for holding either the lateral strap 18 or the medial strap 16 securely against the underliner 12.

Upper leg wrap 22 and lower leg wrap 20 are sewn at the midpoint of each to the back of the underliner 12 at an area roughly corresponding to the wearer's Achilles tendon. The upper and lower leg wraps 22 and 20 are of sufficient length to extend forwardly to overlap the medial and lateral straps when attached to the underliner 12, as well as to overlap the respective free ends of each. Free end 58 of lower leg wrap 20 has a portion of pile material on the interior side thereof, while free end 60 of lower leg wrap 20 has an area of hook material 44 on the outside thereof for mating engagement with the pile material 42 on free end 58. Similarly, upper leg wrap 22 has a free end 62 presenting an inner side having an area of pile material 42 while free end 64 of upper leg wrap 22, as seen in FIG. 5, has an area of hook material 44 along the outside thereof for mating engagement with the pile material of free end 62.

An opening 66 is defined in the heel region 68 so that the ankle wrap 10 hereof may properly conform to the wearer's foot. A heel cup 70 is located forwardly of the opening 66 and may be secured to the underliner 12 by a rivet 72 or snap whereby the heel cup may be removed. The heel cup is provided with two spaced apart forwardly extending hook material strips 74 and 76 for attaching heel counters 78 and 80, respectively, each of which are provided with pile material for ease of attachment and removal from heel cup 70. The heel cup may thereby be easily posted according to the needs of the wearer.

In use, the ankle brace 10 is initially opened along the left and right front margins 24 and 26 and the foot 40 and ankle 28 placed therein by the wearer as shown in FIG. 1. The foot is located so that the underliner 12 extends from the base of the calf to the metatarsal heads of the wearer's foot 40, providing a maximum base of support. The heel of the wearer is then located in the heel cup 70 with counters 78 and 80 placing the foot 40 in an even, neutral position.

When used on the right foot as shown in the drawing, the eight front margin 26 is placed along the wearer's instep with the left front margin wrapping thereover and the instep strap 14 is then affixed to the pile material 42 to effect a first closure region 46 along the instep or metatarsal region of the wearer's foot 40 as shown in FIG. 2. The left front margin 24 along the ankle 28 and lower portion of the wearer's leg 52 is then wrapped over the right front margin to effect a second closure region 50 as shown in FIG. 3. The elastic qualities of the underliner 12 not only provides some padding and protection of the ankle 28 from shock due to contact with other objects but also wraps around the ankle 28 to provide a degree of support.

The lateral strap 18 and the medial strap 16 are then drawn up along the medial and lateral aspects of the foot to provide support for both the medial and lateral ligamentous structures. Both lateral strap 18 and medial strap 16 may be pulled upwardly along the ankle 28 to attach to the respective lateral strap attachment region 56 and medial strap attachment region 54 without imparting torsion to the foot 40 or the ankle 28, or causing undesired inversion (outside of the foot turning toward the arch) or eversion (outside of the foot pivoting upward toward the outside of the ankle) of the foot. The elastic qualities of the underliner 12 which is stretched over the foot 40, ankle 28 and lower leg 52 prevent the foot from shifting relative to the underliner and the medial and lateral straps maintain the foot in a neutral position while allowing limited pivoting of the foot along a vertical plane extending from the heel to the toe and limited rotation of the foot relative to the leg so that walking and other athletic movement may be accomplished.

The ankle 28 and lower leg 50 are provided with additional support by the provision of upper and lower leg wraps 22 and 20. After the wearer has secured the medial and lateral straps in position by attaching their remote ends to the underliner with suitable tension, the lower wrap 20 and the upper wrap 22 are brought forward from the rear of the ankle brace 10 to cover the medial strap 16 and the lateral strap 18 where they are attached to the underliner 12 at medial strap attachment region 54 and lateral strap attachment region 56. The upper wrap 22 and the lower wrap 20 are provided with elastic material so that the may stretch in a circumferential direction around the leg and ankle to provide support thereto and to hold the medial and lateral straps in position. It should be noted that the remote ends of the medial and lateral straps are thus protected from coming loose or being torn off during the course of an athletic contest.

The hook and pile closures described herein are most effective in securing the ankle brace 10 in position and enabling adjustment to apply the necessary tension both linearly, as in the case of the medial and lateral straps, and circumferentially in the case of the elastic undcerliner 12 and the upper leg wrap 22 and the lower leg wrap 20. Thus, the use of hook and pile closures allow greater freedom of adjustment than in most other attachment means.

The ankle brace 10 is thus suitable not only in reducing the possibility of future injury to the ankle 28 but also for preventing injury to a healthy ankle. The brace hereof is capable of use by an athlete with conventional shoes and allows limited but still significant range of motion of the foot.

I claim:

1. An ankle brace for protecting a human ankle comprising:
    an underliner made of stretchable material for receiving and fitting over a wearer's foot and presenting a sole portion at the bottom thereof;
    a lateral strap of flexible relatively inelastic material secured to the sole portion of the underliner and presenting a remote end including means for releasable attachment to said underliner;
    a medial strap of flexible relatively inelastic material secured to the sole portion of the underliner and presenting a remote end having means for releasable attachment to said underliner;
    means located on said underliner relatively proximate the medial side of the ankle for releasably receiving said medial strap in tension thereon; and
    means located on said underliner relatively proximate the lateral size of the ankle for releasably receiving said lateral strap in tension thereon,
    said lateral strap and said medial strap each being secured to said underliner at a common location along the bottom of the sole portion of the underliner for conforming said underliner to the foot and for selectively and alternately positioning and maintaining said foot at a neutral, inverted or everted position.

2. An ankle brace as set forth in claim 2 wherein said remote end of said lateral strap terminates proximate the medial side of the ankle.

3. An ankle brace as set forth in claim 2 wherein said remote end of said lateral strap terminates proximate the lateral side of the ankle.

4. An ankle brace as set forth in claim 3 wherein each said medial strap and said lateral strap are secured to the sole portion of the underliner proximate an arch of the foot joined to the ankle.

5. An ankle brace as set forth in claim 4 including at least one wrap for extending circumferentially around said underliner proximate the lower leg of the wearer in covering relationship to said remote end of said medial strap and said remote end of said proximate strap.

6. An ankle brace as set forth in claim 5 wherein said lateral strap and said medial strap are formed of a unitary strip of relatively inelastic material secured at the midpoint thereof to the sole portion of the underliner.

7. An ankle brace as set forth in claim 6 wherein said underliner extends from the base of the calf to the metatarsal heads of the wearer's foot.

8. An ankle brace as set forth in claim 7 including a strap extending over the underliner proximate the instep of the wearer's foot to stretch and provide tensioning of the underliner in a transverse direction across the foot.

9. An ankle brace as set forth in claim 1, wherein said medial strap and said lateral strap are formed of a single strip of material secured to said underliner at substantially the midpoint thereof.

* * * * *